United States Patent
DeVries et al.

(10) Patent No.: US 6,416,530 B2
(45) Date of Patent: *Jul. 9, 2002

(54) DEVICE AND METHOD FOR SELECTIVELY REMOVING A THROMBUS FILTER

(75) Inventors: Robert B. DeVries, Marlborough; Hannah Shu Kim, Boxborough; Naroun Soun, Lawrence; Forrest D. Whitcher, Allston; Mark W. Wolfson, Framingham, all of MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/904,259

(22) Filed: Jul. 12, 2001

Related U.S. Application Data

(63) Continuation of application No. 09/491,273, filed on Jan. 26, 2000.

(51) Int. Cl.$^7$ .............................................. A61M 29/00
(52) U.S. Cl. ...................................................... 606/200
(58) Field of Search ................................ 606/200, 191, 606/194, 195, 198, 108, 202, 127, 114; 604/96, 104, 93

(56) References Cited

U.S. PATENT DOCUMENTS

| | | | |
|---|---|---|---|
| 3,952,747 A | 4/1976 | Kimmell, Jr. ............ 128/303 R |
| 4,494,531 A | 1/1985 | Gianturco .................... 128/1 R |
| 4,688,553 A | 8/1987 | Metals ........................ 128/1 R |
| 4,727,873 A | 3/1988 | Mobin-Uddin ........... 128/303 R |
| 4,781,177 A | 11/1988 | Lebigot ....................... 128/897 |
| 4,793,348 A | 12/1988 | Palmaz ........................ 128/325 |
| 4,817,600 A | 4/1989 | Herms et al. ............ 128/303 R |
| 5,059,205 A | 10/1991 | El-Nounou et al. ......... 606/200 |
| 5,133,733 A | 7/1992 | Rasmussen et al. ......... 606/200 |
| 5,147,379 A | 9/1992 | Sabbaghian et al. ........ 606/206 |
| 5,174,295 A | 12/1992 | Christian et al. ...... 128/662.06 |
| 5,234,458 A | 8/1993 | Metais ......................... 606/200 |
| 5,242,462 A | 9/1993 | El-Nounou et al. ......... 606/200 |
| 5,324,304 A | 6/1994 | Rasmussen .................. 606/200 |

(List continued on next page.)

*Primary Examiner*—Michael J. Milano
*Assistant Examiner*—Vy Q. Bui
(74) *Attorney, Agent, or Firm*—Crompton, Seager & Tufte LLC

(57) ABSTRACT

A thrombus filter which can be securely fixed in a selected location in the vascular system of a patient and removed when no longer required. The thrombus filter includes a plurality of struts which radiate from a body portion to form the generally conical shape of the thrombus filter. The thrombus filter includes anchor members joined to the free end of each strut. The thrombus filter includes an insulating layer substantially covering the thrombus filter including the body portion, the struts and the anchor members. The insulating layer includes an opening proximate the anchor members. The opening in the insulating layer creates a conductive path between the thrombus filter and the patient's body. When removal of the thrombus filter is desired, a first electrical conductor forms an electrical connection with the body portion of the thrombus filter. A second electrical conductor forms an electrical connection with the patient's body. A power supply is used to selectively apply a voltage differential between the thrombus filter and the body of the patient. This voltage differential induces an electrical current the flow of electrical current between the thrombus filter and the patient's blood causes the electrolytic corrosion of the thrombus filter proximate the opening in the insulating layer. When the bond between the struts of the thrombus filter and the anchors is cut through or weakened, the thrombus filter may be pulled into the lumen of a retrieval catheter. Removal of the thrombus filter from the patient's body is completed by withdrawing the retrieval catheter from the patient's blood vessel.

7 Claims, 5 Drawing Sheets

U.S. PATENT DOCUMENTS

| | | | |
|---|---|---|---|
| 5,344,427 A | 9/1994 | Cottenceau et al. | 606/200 |
| 5,380,320 A | 1/1995 | Morris | 606/33 |
| 5,383,887 A | 1/1995 | Nadal | 606/200 |
| 5,423,829 A * | 6/1995 | Pham et al. | 606/108 |
| 5,522,836 A * | 6/1996 | Palermo | 606/200 |
| 5,540,680 A | 7/1996 | Guglielmi et al. | 606/32 |
| 5,643,254 A * | 7/1997 | Scheldrup et al. | 606/32 |
| 5,669,905 A | 9/1997 | Scheldrup et al. | 606/32 |
| 5,681,347 A | 10/1997 | Cathcart et al. | 606/200 |
| 5,709,704 A | 1/1998 | Nott et al. | 606/200 |
| 5,911,704 A | 6/1999 | Humes | 604/93 |
| 6,036,720 A * | 3/2000 | Abrams et al. | 606/213 |
| 6,067,491 A | 5/2000 | Takahashi | 701/37 |
| 6,086,577 A * | 7/2000 | Ken et al. | 606/1 |
| 6,217,600 B1 * | 4/2001 | DiMatteo | 606/200 |

* cited by examiner

*Fig. 2*
*Fig. 3*
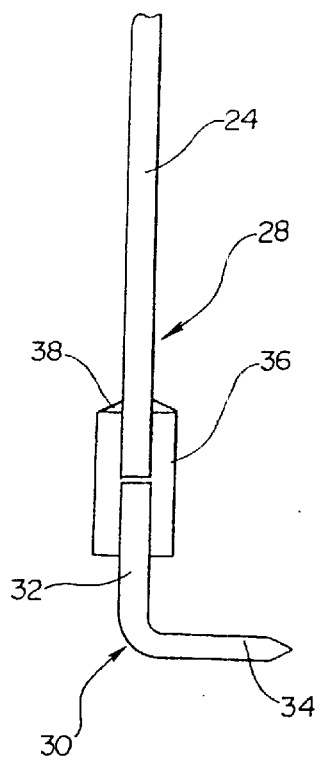
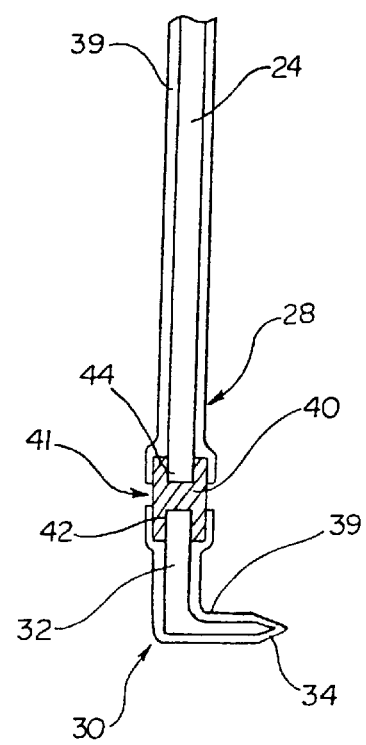

DEVICE AND METHOD FOR SELECTIVELY REMOVING A THROMBUS FILTER

This is a continuation of copending application Ser. No. 09/491,273 filed on Jan. 26, 2000.

FIELD OF THE INVENTION

The present invention relates generally to filters for use inside blood vessels. More particularly, the present invention relates to thrombus filters which can be securely affixed at a selected location in the vascular system and removed when no longer required.

BACKGROUND OF THE INVENTION

There are a number of situations in the practice of medicine when it becomes desirable for a physician to place a filter in the vascular system of a patient. One of the most common applications for vascular filters is the treatment of Deep Venous Thrombosis (DVT). Deep Venous Thrombosis patients experience clotting of blood in the large veins of the lower portions of the body. These patients are constantly at risk of a clot breaking free and traveling via the inferior vena cava to the heart and lungs. This process is known as pulmonary embolization. Pulmonary embolization can frequently be fatal, for example when a large blood clot interferes with the life-sustaining pumping action of the heart. If a blood clot passes through the heart it will be pumped into the lungs and may cause a blockage in the pulmonary arteries. A blockage of this type in the lungs will interfere with the oxygenation of the blood causing shock or death.

Pulmonary embolization may be successfully prevented by the appropriate placement of a thrombus filter in the vascular system of a patient's body. Placement of the filter may be accomplished by performing a laparotomy with the patient under general anesthesia. However, intravenous insertion is often the preferred method of placing a thrombus filter in a patient's vascular system.

Intravenous insertion of a thrombus filter is less invasive and it requires only a local anesthetic. In this procedure, the thrombus filter is collapsed within a delivery catheter. The delivery catheter is introduced into the patients vascular system at a point which is convenient to the physician. The delivery catheter is then fed further into the vascular system until it reaches a desirable location for filter placement. The thrombus filter is then released into the blood vessel from the delivery catheter.

In the treatment of Deep Venous Thrombosis, a thrombus filter is placed in the inferior vena cava of a patient. The inferior vena cava is a large vessel which returns blood to the heart from the lower part of the body. The inferior vena cava may be accessed through the patient's femoral vein.

Thrombus filters may be placed in other locations when treating other conditions. For example, if blood clots are expected to approach the heart and lungs from the upper portion of the body, a thrombus filter may be positioned in the superior-vena cava. The superior vena cava is a large vessel which returns blood to the heart from the upper part of the body. The superior vena cava may by accessed through the jugular vein, located in the patient's neck.

Once placed inside a blood vessel, a thrombus filter acts to catch and hold blood clots. The flow of blood around the captured clots allows the body's lysing process to dissolve the clots.

The walls of the blood vessels are lined with a thin inner membrane or intima. When the anchor portions of a thrombus filter puncture this inner membrane the body responds in a process referred to as neointimal hyperplasia. As a result, the punctured area of inner membrane is overgrown with a number of new cells. The anchor portions of the thrombus filter are encapsulated with new cell growth (neointimal hyperplasia).

Due to neointimal hyperplasia, thrombus filters placed in the blood vessel of a patient become affixed in the blood vessel walls within two weeks after being implanted. Because the portions of the filter contacting the blood vessel wall become fixed in this way, many prior art filters cannot be removed percutaneously after being in place for more than two weeks.

SUMMARY OF THE INVENTION

The present invention pertains to a thrombus filter and a method of removing a thrombus filter using minimally invasive methods while limiting complications due to neointimal encapsulation of the anchor portions of the thrombus filter. A thrombus filter for use with the inventive removal method includes a body member and a plurality of elongated struts. Each strut has a joined end and a free end. The joined end of each strut is fixably attached to the body member on the thrombus filter. The struts radiate outwardly from the body member of the thrombus filter such that the thrombus filter is generally conical in shape. A thrombus filter includes an insulating layer substantially covering the thrombus filter including the body portion, struts, and anchor members. The insulation layer includes an opening. In one embodiment of the current invention, the opening in the insulation layer is proximate a sacrificial link. The opening in the insulation layer allows direct contact between a portion of the thrombus filter and the patient's blood. This direct contact creates a conductor path between the thrombus filter and the body of the patient.

When removal of a thrombus filter is desired, a first electrical conductor forms an electrical connection with the body portion of the thrombus filter. A second electrical connector forms an electrical connection with the patient's body. A power supply is used to selectively apply a voltage differential between the body portion of the thrombus filter and the body of a patient. This voltage differential induces a current through the thrombus filter.

When a voltage differential is applied between the body portion of the thrombus filter and the body of a patient, current flows between the thrombus filter and the patient's blood at a location proximate the opening in the insulating layer. The flow of electrical current between the thrombus filter and the patient's blood causes electrolytic corrosion of the thrombus filter in a selected area. The current flow is continued until a selected area of the thrombus filter has been weakened or cut through by electrolytic corrosion. In one embodiment of the thrombus filter, electrolytic corrosion weakens or cuts through a sacrificial link holding an anchor to the thrombus filter.

When the thrombus filter is deployed inside a blood vessel, the free ends of the struts engage the blood vessel wall. The body member of the thrombus filter is held in a position proximate the center of the blood vessel by the plurality of struts which engage the blood vessel walls with opposing force vectors. The conical formation of struts acts to trap or capture blood clots. The generally conical shape of the formation of struts, serves to urge captured blood clots toward the center of the blood flow. The flow of blood around the captured blood clots allows the body's natural lysing process to dissolve the clots.

To assure firm attachment of the thrombus filter to the blood vessel, anchor members may be attached to the free ends of the struts. In one embodiment of the thrombus filter, anchors are attached by a sleeve. In a second embodiment of the thrombus filter, anchor members are attached by a sacrificial link. In a third embodiment of the thrombus filter, the anchors are formed from the strut itself.

When anchor members are attached by a sacrificial link, the material of the sacrificial link is selected to be one which is susceptible to electrolytic disintegration in blood. The thrombus filter includes an insulating layer substantially covering the thrombus filter including the body portion, the struts and the anchor members. An opening in the insulation layer is selectively created over a portion of the thrombus filter which retains anchors to the free ends of the struts. This opening in the insulating layer allows direct contact between the material of the thrombus filter and the patient's blood. This direct contact creates a conductive path between a portion of the thrombus filter and the patient's blood.

When removal of the thrombus filter is desired, a removal catheter with a lumen and a distal end is disposed in the lumen of the blood vessel. The removal catheter enters the patient's vascular system at a point which is readily accessible to the physician. Once in the vascular system, the catheter is urged forward until the distal end of the removal catheter is proximate the thrombus filter. A first electrical conductor is disposed inside the lumen of the removal catheter. The first electrical conductor includes a proximal end and a distal end. The distal end of the first electrical connector penetrates the insulating layer on the thrombus filter to form an electrical connection with the body portion of the thrombus filter. The proximal end of the first electrical conductor is electrically connected to a power supply. A proximal end of the second electrical conductor is also electrically connected to the power supply. The distal end of the second electrical conductor is electrically connected to the body of the patient.

The power supply is used to selectively apply a voltage differential between the first electrical conductor and the second electrical conductor. This voltage differential induces a current flow between the thrombus filter and the blood of the patient. Because the thrombus filter is covered with an insulating layer, this current must flow through the area proximate the opening in the insulating layer. The flow of current causes electrolytic corrosion of the thrombus filter in the selected area. The flow of electrical current between the thrombus filter and the patient's blood is continued until a selected portion of the thrombus filter has been weakened or cut completely free by electrolytic corrosion. The weakened link will separate when a load is applied, for example, by an elongated pulling tool.

When the anchor portions of the thrombus filter are separated in this fashion, the thrombus filter may be pulled into the lumen of the retrieval catheter leaving the anchor portions attached to the blood vessel wall. Pulling the thrombus filter into the lumen of the retrieval catheter causes the struts to collapse. When the struts collapse, the thrombus filter is transformed from a generally conical shape to a generally cylindrical shape. Pulling of the thrombus filter into the lumen of the retrieval catheter may be accomplished with a retrieval wire including a hook. The anchor members remain fixed in the walls of the blood vessel by encapsulating cell growth due to neointimal hyperplasia. When the thrombus filter is pulled into the lumen of the retrieval catheter, the removal of the thrombus filter from the patient becomes simply a matter of withdrawing the removal catheter from the lumen of the blood vessel.

BRIEF DESCRIPTION OF THE DRAWINGS

FIG. 2 is a plan view of a portion of the thrombus filter including an anchor portion and a weakened strut portion;

FIG. 3 is a plan view of a portion of a thrombus filter including an anchor portion and a weakened strut portion;

DETAILED DESCRIPTION OF THE INVENTION

Figure 1:
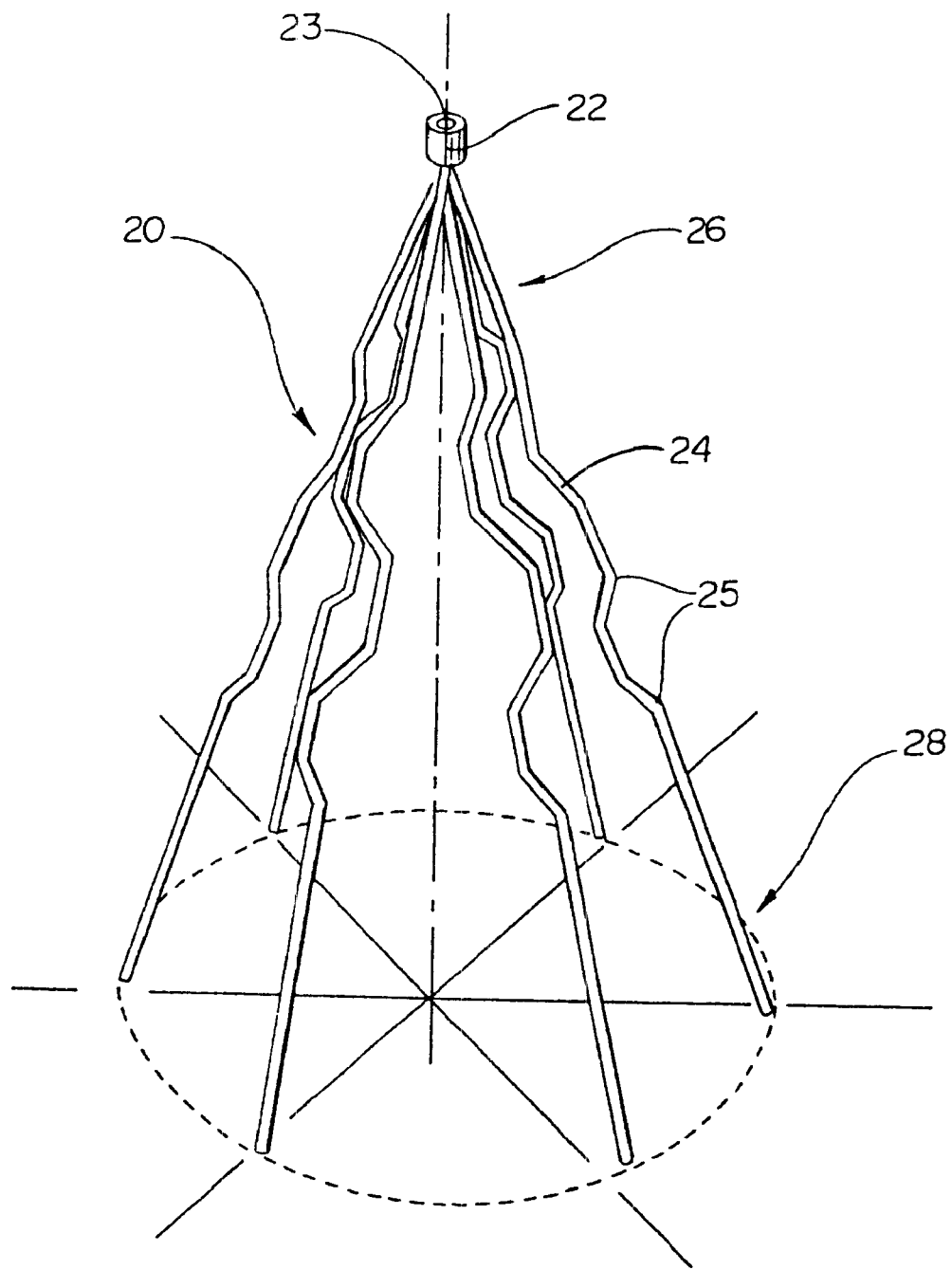
FIG. 1 is a perspective view of a thrombus filter.

FIG. 1 is a perspective view of a thrombus filter 20. Thrombus filter 20 includes a body member 22 and a plurality of elongated struts 24. Struts 24 each have a joined end 26 and a free end 28. Joined end 26 of each strut 24 is fixedly attached to body member 22.

Struts 24 may be fabricated from wire with a circular or rectangular cross section. For example, struts 24 may be comprised of 2 inch lengths of 0.018" diameter wire. Stainless steel, titanium, and nickel-titanium alloys have all been found to be acceptable materials for struts 24. In the embodiment of FIG. 1, a plurality of bends 25 are disposed between free end 28 and fixed end 26 of each strut 24. It should be understood that struts 24 may also be straight, or include bends different than those illustrated in FIG. 1, without departing from the spirit or scope of the present invention.

In the embodiment of FIG. 1, body member 22 is generally cylindrical in shape, and includes a bore 23. It should be understood that other embodiments of body member 22 are possible without departing from the spirit or scope of the present invention.

Struts 24 radiate outwardly from body member 22 such that thrombus filter 20 is generally conical in shape. When thrombus filter 20 is deployed inside a blood vessel, free ends 28 engage the blood vessel wall. Body member 22 is held in a position. proximate to the center of the blood vessel by the plurality of struts 24 which engage the blood vessel walls with opposing force vectors.

When thrombus filter 20 is disposed in a blood vessel, the conical formation of struts 24 acts to trap, or capture blood clots. The generally conical shape of the formation of struts 24 serves to urge captured blood clots toward the center of the blood flow. The flow of blood around the captured blood clots allows the body's natural lysing process to dissolve the clots.

To assure firm attachment of thrombus filter 20 to the blood vessel, anchor members may be attached to free ends 28 of struts 24. FIG. 2 illustrates one embodiment of an anchor member 30 including a stem 32 and a sharp projection 34. Stem 32 of anchor member 30 is attached to strut 24 with a sleeve 36.

In FIG. 2, sleeve 36 is fixedly attached to free end 28 of strut 24 with a weld joint 38. Other methods of attachment may be used without departing from the spirit or scope of this invention. For example, sleeve 36 may be fixedly attached to free end 28 of strut 24 through soldering, brazing, crimping, or swaging. Sleeve 36 could also be attached to strut 24 with a fastening means such as a suture. Finally, sleeve 36 could be bonded to strut 24 with a permanent adhesive.

Stem 32 is adapted to releasably mate with sleeve 36. The method of connecting stem 32 to sleeve 36 is selected so that the mechanical strength of the connection between sleeve 36 and stem 32 will be less than the mechanical strength of the connection between sleeve 36 and strut 24. Several methods of accomplishing this releasable connection have been contemplated. For example, the outer diameter of stem 32 and the inside diameter of sleeve 36 may be selected to form an interference fit. In another embodiment of the present invention, an adhesive may be used to attach stem 32 to sleeve 36, this adhesive would be selected so that the connection between stem 32 and sleeve 36 would be weaker than the connection between strut 24 and sleeve 36.

When thrombus filter 20 is removed from the body an extraction catheter including an elongated pulling tool is used to exert a pulling force on thrombus filter 20. Thrombus filter 20 is pulled with a force which is sufficient to separate stem 32 from sleeve 36. Thereby removing thrombus filter 20 from the blood vessel, but leaving anchor members 30 attached to the blood vessel wall.

FIG. 3 illustrates an alternate embodiment of the present invention. An anchor member 30 includes a stem 32 and a sharp projection 34. Stem 32 of anchor member 30 is attached to free end 28 of strut 24 with a sacrificial link 40 which is comprised of a material which is susceptible to electrolytic disintegration/weakening in blood. Sacrificial link 40 includes a first bore 42 and a second bore 44.

In the embodiment illustrated in FIG. 3, a first interference fit is formed between stem 32 of anchor member 30 and first bore 42 of sacrificial link 40. A second interference fit may also be formed between free end 28 of strut 24 and second bore 44 of sacrificial link 40. Alternately, free end 28 of strut 24 may be attached to sacrificial link 40 using other methods. For example, sacrificial link 40 may be fixedly attached to free end 28 of strut 24 through soldering, brazing, crimping, or swaging. Sacrificial link could also be attached to strut 24 with a fastening means such as a suture. Finally, sacrificial link 40 could be bonded to strut 24 with an adhesive.

In FIG. 3 it can be appreciated that thrombus filter 20 can be formed from the struts 24 shown in FIG. 3 as an alternative to those shown in FIG. 2. This alternative embodiment of thrombus filter 20 can include an insulating layer 39 substantially covering thrombus filter 20 including body portion 22, struts 24, and anchor members 30 (thrombus filter 20 and body portion 22 not shown in FIG. 3). In FIG. 3, insulating layer 39 is shown covering strut 24, anchor member 30, and a portion of sacrificial link 40. Insulation layer 39 includes an opening 41 proximate sacrificial link 40. Opening 41 of insulating layer 39 allows direct contact between sacrificial link 40 and the patients blood. This direct contact creates a conductive path between sacrificial link 40 and the body of the patient. The significance of this conductive path will be described below.

A number of materials are suitable for use in insulating layer 39, these materials include fluoropolytetrafluoroethylene (PTFE), polyethylene(PE), polypropylene (PP), polyvinylchloride (PVC), and polyurethane. A number of manufacturing processes may be used to create insulating layer 39. For example, a portion of insulating layer 39 may be made up of sections of shrink tubing. The shrink tubing sections may be positioned over the struts then shrunk by the application of heat. A spray process may also be used to apply insulating layer 39 to thrombus filter 20. For example, spraying PTFE solids in a suitable solvent carrier is a process which has been found suitable for this application.

Another material which may be used to fabricate insulating layer 39 is a thermoplastic generically known as parylene. There are a variety of polymers based on para-xylylene. These polymers are typically placed onto a substrate by vapor phase polymerization of the monomer. Parylene N coatings are produced by vaporization of a di(P-xylylene)dimer, pyrollization, and condensation of the vapor to produce a polymer that is maintained at comparatively lower temperature. In addition to parylene-N, parylene-C is derived from di(monochloro-P-xylylene) and parylene-D is derived from di(dichloro-P-xylylene). There are a variety of known ways to apply parylene to substrates. The use of paralene in surgical devices has been disclosed in U.S. Pat. No. 5,380,320 (to J. R. Morris), in U.S. Pat. No. 5,174,295 (to Christian et al.), and in U.S. Pat. No. 6,067,491 (to Taylor et al.).

Figure 4:
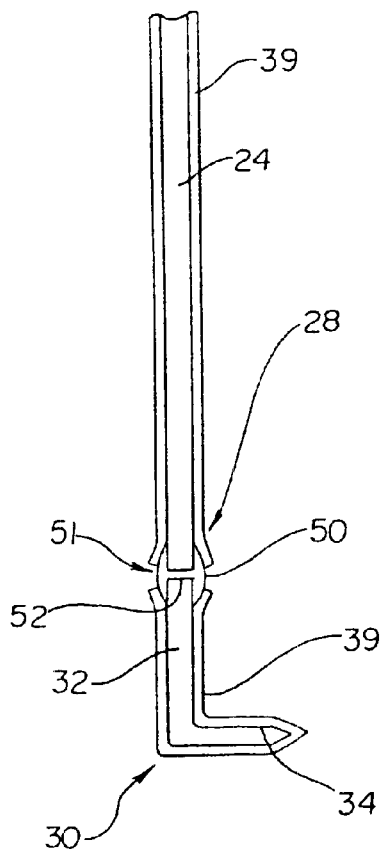
FIG. 4 is a plan view of a portion of a thrombus filter including an anchor portion and a weakened strut portion.

FIG. 4 illustrates an additional embodiment of the present invention. In this embodiment, a distal end 52 of stem 32 is positioned adjacent to free end 28 of strut 24 in a butt joint configuration. Distal end 52 of stem 32 is fixedly joined to free end 28 of strut 24 with a sacrificial link 50. Sacrificial link 50 may be created using a process similar to brazing or soldering. The filler metal used in this process would be one selected because it is susceptible to electrolytic disintegration/weakening in blood.

In FIG. 4 it can be appreciated that thrombus filter 20 can be formed from the struts 24 shown in FIG. 4 as an alternative to those shown in FIG. 2. This alternative embodiment of thrombus filter 20 can include an insulating layer 39 substantially covering thrombus filter 20 including body portion 22, struts 24, and anchor members 30 (thrombus filter 20 and body portion 22 not shown in FIG. 4) In FIG. 4, insulating layer 39 is shown covering strut 24, anchor member 30, and a portion of sacrificial link 50. Insulation layer 39 includes opening 51 proximate sacrificial link 50. Opening 51 of insulating layer 39 allows direct contact between sacrificial link 50 and the patient's body. Specifically, blood and tissue of the patients body is free to contact sacrificial link 50. This direct contact creates a conductive path between sacrificial link 50 and the body of the patient.

Figure 5:
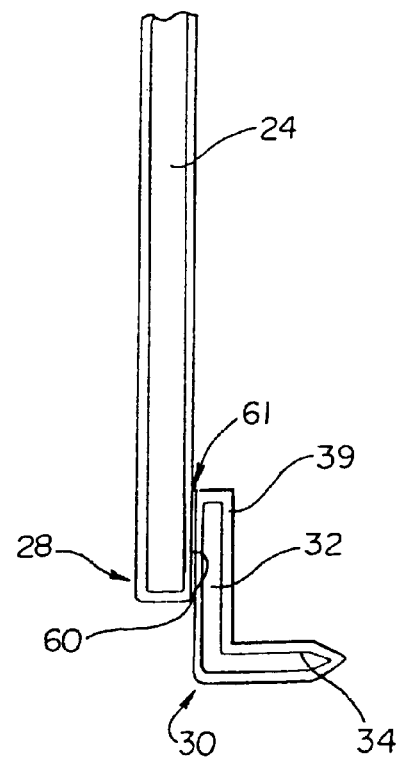
FIG. 5 is a plan view of a portion of a thrombus filter illustrating attachment of an anchor portion to a strut portion.

FIG. 5 illustrates an additional embodiment of the present invention. In this embodiment, stem 32 of anchor 30 is positioned parallel to strut 24 in a lap joint configuration. Stem 32 of anchor member 30 is fixedly joined to strut 24 by a sacrificial link 60. As in the previous embodiment, sacrificial link 60 may be created using a process similar to brazing or soldering. The filler metal used in this process would be one which is susceptible to electrolytic disintegration/weakening in blood.

In FIG. 5 it can be appreciated that thrombus filter 20 can be formed from the struts 24 shown in FIG. 5 as an alternative to those shown in FIG. 2. This alternative embodiment of thrombus filter 20 can include an insulating layer 39 substantially covering thrombus filter 20 including body portion 22, struts 24, and anchor members 30 (thrombus filter 20 and body portion 22 not shown in FIG. 5) In FIG. 5, insulating layer 39 is shown covering strut 24, anchor member 30, and a portion of sacrificial link 60. Insulation layer 39 includes opening 61 proximate sacrificial link 60. Opening 61 of insulating layer 39 allows direct contact between sacrificial link 60 and the patient's blood. This direct contact creates a conductive path between sacrificial link 60 and the body of the patient. The significance of this conductive path is described in the following paragraph.

The embodiments shown in FIGS. 3, 4, and 5 include a sacrificial link comprised of a material which is susceptible to electrolytic disintegration/weakening in blood. When it is desirable to remove thrombus filter 20 from a blood vessel, an electrical current is passed through sacrificial links 40, 50, 60. This electrical current causes sacrificial links 40, 50, 60 to corrode, dissolve, or disintegrate until the bond between free end 28 of strut 24 and stem 32 of anchor 30 is broken or weakened.

Figure 6:
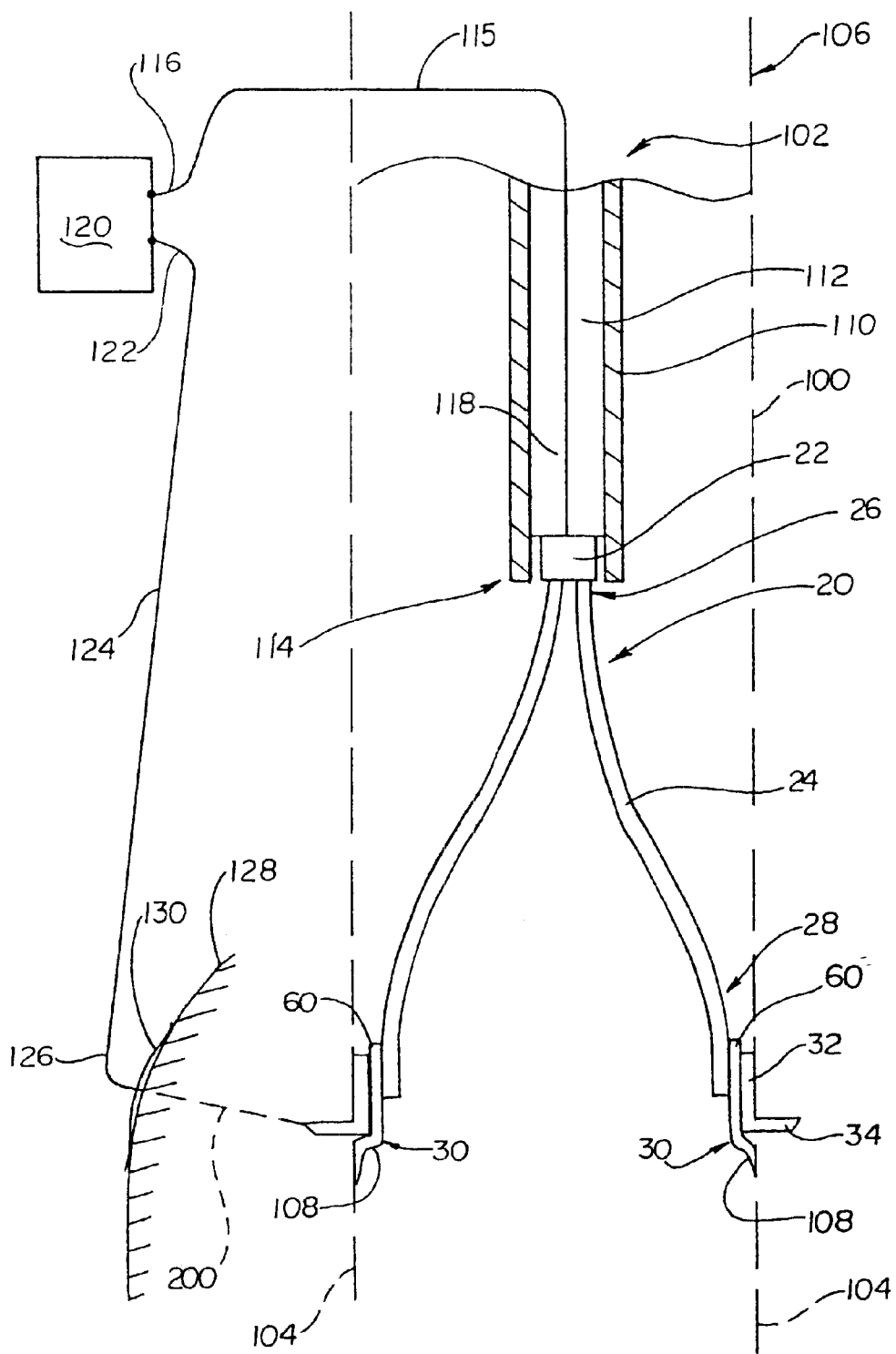
FIG. 6 is a schematic representation of the removal of a thrombus filter from a blood vessel.

FIG. 6 schematically illustrates a thrombus filter 20 disposed in a lumen 102 of blood vessel 100. As described previously, joined ends 26 of struts 24 are fixedly joined to body portion 22. Free ends 28 of struts 24 are fixedly attached to anchors 30 by sacrificial links 60.

Blood vessel 100 includes walls 104 having a thin inner membrane or intima 106. Anchors 30 have punctured inner membrane 106 and are embedded in walls 104 of blood vessel 100. The body responds to the puncturing of inner membrane 106 with a process referred to as neointimal hyperplasia. The punctured area of inner membrane 106 is overgrown with a multitude of new cells. In FIG. 6, these new cells are illustrated as encapsulating cell growth 108. Within about 2 to 3 weeks after a thrombus filter is implanted, anchors 30 will be completely encapsulated by encapsulating cell growth 108. With many prior art thrombus filters, removal of the filter after neointimal hyperplasia encapsulation has occurred is very difficult, if not impossible.

A preferred embodiment of the thrombus filter in accordance with the present invention can be removed using minimally invasive methods without complications due to neointimal hyperplasia of anchors 30. A minimally invasive process which may be used to remove thrombus filter 20 from blood vessel 100 is schematically represented in FIG. 6.

A removal catheter 110 with a lumen 112 and a distal end 114 is disposed in lumen 102 of blood vessel 100. Removal catheter 110 enters the patients vascular system at a point which is readily accessible to the physician. Once in the vascular system, catheter 110 is urged forward until distal end 114 is proximate to the thrombus filter 20.

A first electrical conductor 115 is disposed inside lumen 112 of-removal catheter 110. First electrical conductor 115 includes a proximal end 116 and a distal end 118. Distal end 118 of first electrical conductor 115 has penetrated insulating layer 39 (not shown) to form an electrical connection with body portion 22 of thrombus filter 20. Proximal end 116 of first electrical conductor 115 is electrically connected to a power supply 120. A proximal end 122 of a second electrical conductor is also electrically connected to power supply 120. A distal end 126 of second electrical conductor 124 is electrically connected to an area of exposed skin 128 of a living being. The connection between second electrical conductor 124 and skin 128 is preferably made via an electrode 130.

A number of methods suitable for forming the electrical connection between first electrical connector 114 and body portion 22 of thrombus filter 20 are known in the art. For example, a needle electrode could be disposed at distal end 118 of electrical connector 114. The needle electrode could penetrate insulating layer 39 and make electrical contact with body portion 22 of thrombus filter 20. An easily deformed material such as silicone rubber or silicone foam rubber could be disposed around the needle electrode to insulate the electrical connection.

Power supply 120 is used to selectively apply a voltage differential between first electrical conductor 114 and second electrical conductor 124. This voltage differential induces a current flow 200 through sacrificial links 60 (links 40 and 50 could be sacrificed in this manner as well). In FIG. 6, the path which current flow 200 takes through the body of the patient is represented by a dashed link. Current flow 200 causes sacrificial links 60 to corrode, dissolve, or disintegrate until the bond between free end 28 of strut 24 and stem 32 of anchor 30 are broken or weakened. When the bonds between struts 24 and anchors 30 is broken or weakened, thrombus filter 20 may be pulled into lumen 112 of retrieval catheter 110.

Figure 7:
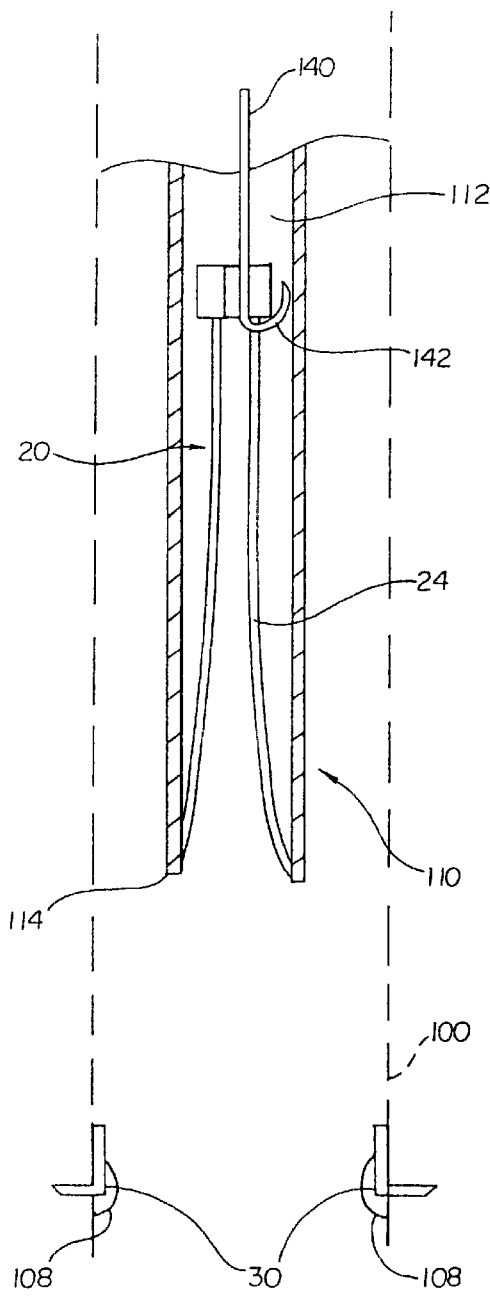
FIG. 7 is a schematic illustration of a thrombus filter which has been pulled into the lumen of a retrieval catheter.

FIG. 7 is a schematic representation of thrombus filter 20 after it has been pulled into lumen 112 of retrieval catheter 110. As may be seen in FIG. 7, pulling thrombus filter 20 into lumen 112 of retrieval catheter 110 causes struts 24 to collapse. When struts 24 collapse thrombus filter 20 is transformed from a generally conical shape to a generally cylindrical shape. The pulling of thrombus filter 20 into lumen 112 of retrieval catheter 110 may be accomplished with a retrieval wire 140 including a hook 142. As can also be seen in FIG. 7, anchor members 30 remain fixed in the walls of blood vessel 100 by encapsulating cell growth 108. When thrombus filter 20 is pulled into lumen 112 of retrieval catheter 110, the removal of thrombus filter 20 from the patient becomes a simple matter of withdrawing removal catheter 110 from lumen 102 of blood vessel 100.

Figure 8:
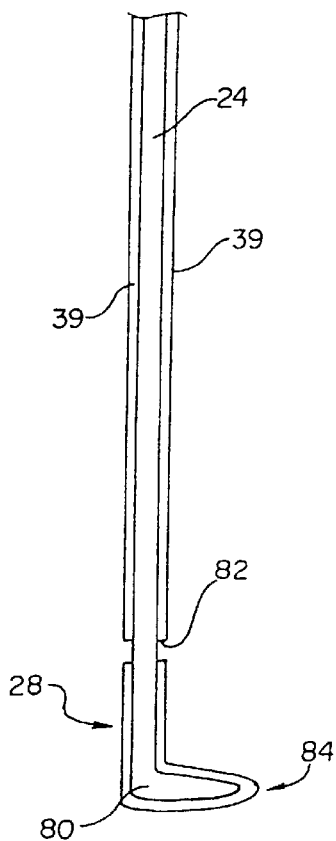
FIG. 8 is a plan view of a portion of the thrombus filter.

FIG. 8 illustrates an additional embodiment of the present invention. In this embodiment, free end 28 of strut 24 includes a bend 80 and a sharp projection 84. Bend 80 and sharp projection 84 enable free end 28 of strut 24 to anchor thrombus filter 20 into the walls of a blood vessel. Strut 24 substantially covered with a layer of insulating material 39. A thrombus filter 20 of the embodiment shown in FIG. 8 includes an insulating layer 39 substantially covering thrombus filter 20 including body portion 22 (not shown) and struts 24. Insulation layer 39 includes an opening 82 proximate free end 28 of strut 24. Opening 82 of insulating layer 39 allows direct contact between strut 24 and the patient's blood. This direct contact creates a conductive path between strut 24 and the body of the patient.

The embodiment of FIG. 8 may be removed using a process similar to that shown in FIG. 6. A first electrical conductor forms an electrical connection with the body portion of the thrombus filter. A second electrical conductor forms an electrical connection with the patient's body. This connection may be via an electrode placed on the patient's skin as shown in FIG. 6. It should be understood that the electrical connection to the patient's body may be accomplished using other methods without departing from the spirit or scope of the invention. For example, the connection to the patients body may be made through an electrode disposed on the retrieval catheter which makes direct contact with the patient's blood.

A power supply is used to selectively apply a voltage differential between the body portion of the thrombus filter and body of the patient. This voltage differential induces a current flow through the thrombus filter. In the embodiment of FIG. 8, current flows between strut 24 and opening 82 in insulating layer 39.

The flow of electrical current between strut 24 and the patients blood causes the electrolytic corrosion of strut 24 in an area proximate opening 82 in insulating layer 39. The current flow is continued until strut 24 has been weakened or cut through by electrolytic corrosion. To reduce the time required for the removal of thrombus filter 20, the cross sectional area of strut 24 may be reduced proximate opening 82 in insulating layer 39. When struts 24 of thrombus filter 20 are weakened or cut through, thrombus filter 20 may be pulled into a retrieval catheter.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A thrombus filter configured for placement within a blood vessel lumen defined by a blood vessel wall, comprising:

filter means for filtering emboli from blood;
   an anchor member including a sharp projection; and
   means for releasably attaching the anchor member to the filter means such that the anchor member can be detached from the filter means within the vessel.

2. The thrombus filter of claim 1, wherein the filter means includes a plurality of struts.

3. The thrombus filter of claim 2, wherein the struts have a circular cross section.

4. The thrombus filter of claim 1, wherein the means for releasably attaching includes means for attaching by interference fit.

5. The thrombus filter of claim 4, wherein the means for attaching includes a sleeve.

6. The thrombus filter of claim 1, wherein the means for attaching includes a weld joint.

7. The thrombus filter of claim 1, wherein the means for attaching includes a solderjoint.

* * * * *

UNITED STATES PATENT AND TRADEMARK OFFICE
CERTIFICATE OF CORRECTION

PATENT NO. : 6,416,530 B2
DATED : July 9, 2002
INVENTOR(S) : Robert B. DeVries et al.

It is certified that error appears in the above-identified patent and that said Letters Patent is hereby corrected as shown below:

<u>Title page,</u>
Item [75], Inventors, delete "Naroun Soun" and insert -- Naroun Suon --

Signed and Sealed this

Twenty-fifth Day of March, 2003

JAMES E. ROGAN
*Director of the United States Patent and Trademark Office*